United States Patent [19]

Sakamoto et al.

[11] Patent Number: 5,308,827
[45] Date of Patent: May 3, 1994

[54] HERBICIDAL FOAM COMPOSITION

[75] Inventors: Naoki Sakamoto; Osamu Sudo, both of Hiroshima; Tomoko Shomura; Youko Inoue, both of Kanagawa, all of Japan

[73] Assignees: Fumakilla Limited; Meiji Seika Kaisha, Ltd., both of Tokyo, Japan

[21] Appl. No.: 21,569

[22] Filed: Feb. 24, 1993

Related U.S. Application Data

[63] Continuation-in-part of Ser. No. 798,935, Nov. 27, 1991, abandoned.

[30] Foreign Application Priority Data

Nov. 28, 1990 [JP] Japan ................... 2-322601
Nov. 1, 1991 [JP] Japan ................... 3-313116

[51] Int. Cl.⁵ .............................. A01N 57/04
[52] U.S. Cl. ....................... 504/206; 504/116; 71/900; 71/DIG. 1
[58] Field of Search .......... 504/116, 201, 205, 206; 71/DIG. 1, 900

[56] References Cited

U.S. PATENT DOCUMENTS

| | | | |
|---|---|---|---|
| 3,689,245 | 9/1972 | Weidman et al. | 71/65 |
| 3,692,512 | 9/1972 | Sachnik | 71/65 |
| 3,799,758 | 3/1974 | Franz | 504/206 |
| 4,168,963 | 11/1979 | Rupp et al. | 504/205 |
| 4,309,208 | 1/1982 | Takematsu et al. | 504/205 |
| 4,975,425 | 12/1990 | Barnett, Jr. | 514/119 |
| 4,997,592 | 3/1991 | Woogerd | 504/116 |

FOREIGN PATENT DOCUMENTS

| | | |
|---|---|---|
| 3002053 | 8/1980 | Fed. Rep. of Germany . |
| 1272551 | 8/1960 | France . |
| 49-101539 | 1/1974 | Japan . |
| 61-500357 | 3/1986 | Japan . |
| 62-502194 | 8/1987 | Japan . |
| 1449768 | 9/1976 | United Kingdom . |

OTHER PUBLICATIONS

Ohno et al., Chemical Abstracts, vol. 81, No. 14, 1974, abstract No. 82248w.
Uchida, Chemical Abstracts, vol. 113, No. 13, 1990, abstract No. 114306m.
Murakami, Chemical Abstracts, vol. 114, No. 15, 1991, abstract No. 142217x.
Chemical Patents Index, Basic Abstracts Journal, Section Ch, Week 9012, Class C, abstract No. 088572(12), (1990).

*Primary Examiner*—Allen J. Robinson
*Assistant Examiner*—Brian G. Bembenick
*Attorney, Agent, or Firm*—Banner, Birch, McKie and Beckett

[57] ABSTRACT

This invention relates to a herbicidal foam composition comprising, on the basis of the total weight of the composition, (a) a herbicide selected from the group consisting of Bialaphos, Glufosinate, Glyphosate and a mixture thereof, (b) an anionic and/or nonionic surfactant(s), (c) a solvent, (d) a foam controlling agent selected from the group consisting of silicone oil, a $C_1$-$C_{10}$ alcohol and a mixture thereof, (e) water as a diluent and (f) liquefied petroleum gas as a propellant, the pH of said composition being adjusted to within about 3-11.

8 Claims, No Drawings

HERBICIDAL FOAM COMPOSITION

REFERENCE TO RELATED APPLICATION

This is a continuation-in-part of the pending patent application, Ser. No. 798,935 filed Nov. 27, 1991, entitled "Foam-forming Herbicidal Composition and Method of Application", which is now abandoned.

BACKGROUND OF THE INVENTION

1. Field of the Invention

The present invention relates to a herbicidal foam composition, particularly an emulsion foam composition, having fine bubbles and fluidity.

2. Description of the Prior Art

Conventional herbicides may be classified into solid- and liquid-formulations. Each type has both advantages and disadvantages. Granules, powders, plates, and sticks are applied as solids. Water soluble powders, emulsifiable concentrates, wettable powders, concentrated solutions, flowable formulations and AL-agents (already diluted to a concentration suitable for use) are applied in liquid-formulations. Aerosol herbicidal compositions have also been developed. For example, a liquid herbicidal composition comprising a certain organic herbicide and a propellant is described in Japanese Patent Public Disclosure No. 49-101539.

As mentioned above, all conventional solid and liquid herbicidal compositions such as granules, powders, plates, sticks, aqueous solutions, emulsions, hydrates, solutions, flowable agents and AL-agents, have both advantages and disadvantages, as will be explained below.

Solid herbicidal compositions, which can be applied without dilution or other preparation, are easy to use. Dosage, however, is not always clear because of the difficulty in providing exact measurements in small-scale operations such as domestic use. It is also difficult to scatter a solid herbicide uniformly.

Most liquid herbicides have the advantage that they can be sprinkled uniformly with a watering can. They are prepared in concentrated form and must be diluted before use. This dilution sometimes causes the dosage to be unexact and prevents proper application in small-scale operations such as domestic use. Also, it is necessary to rinse out the apparatus or containers after use. Liquid herbicides used for the treatment of stems and leaves have another disadvantage in that a large portion of the sprinkled solution flows down to the ground resulting in a great waste of the active agent.

Aerosols are very convenient and require no dilution or rinsing. A large portion of sprayed aerosol, however, also flows down to the ground resulting in a great waste of the active agent. This fact also causes difficulty in visually determining which areas have been treated. Since sprayed particles are small and easily scattered, valuable plants may be damaged and humans and animals, especially the user, may be exposed to harmful inhalation of the active ingredients of the herbicide.

Thus a proper form of administration of herbicides has been desired for small-scale operations such as domestic use.

Herbicidal foam compositions are known. However, conventional foam herbicides have problems, both in volatility, viscosity, fluidity, compatibility and water-solubility of the liquid before being confined in an aerosol-container equipped with a propelling apparatus (hereinafter referred to as "the original liquid"), and in retention time of the foam, leaf depositing properties and herbicidal effects after forming a foam.

SUMMARY OF THE INVENTION

Therefore an object of the present invention is to provide a herbicidal foam composition which overcomes the above-mentioned drawbacks and which has the advantage that already-treated areas can easily be visually distinguished from untreated parts.

Another object of the present invention is to provide a herbicidal foam composition which can readily be utilized efficiently and safely.

The herbicidal foam composition of the present invention comprises, on the basis of the total weight of the composition, (a) about 0.05 to 20% of a herbicide selected from the group consisting of Bialaphos, Glufosinate, Glyphosate and a mixture thereof, (b) about 0.1 to 10% of an anionic and/or nonionic surfactant(s), (c) about 0.1 to 20% of a solvent, (d) about 0.002 to 21% of a foam controlling agent selected from the group consisting of silicone oil, a $C_1$-$C_{10}$ alcohol and a mixture thereof, (e) up to about 90% of water as a diluent and (f) up to about 50% of liquefied petroleum gas as a propellant, the pH of said composition being adjusted to within about 3-11.

The compositions of the present invention exhibit the advantages of both solid and liquid preparations due to the hardness of viscosity of foam, and overcome the problems of aerosol preparations. Since the present compositions are capable of being formed into a foam having fine bubbles and fluidity in use, it is easy to determine which areas have been treated.

The herbicide as used in the present invention is a herbicide selected from the group consisting of Bialaphos, Glufosinate, Glyphosate and a mixture thereof, each of which is water-soluble and sprinkled onto stems and leaves.

Each of the herbicides mentioned above can be used alone or in combination. The concentration of each herbicide is within the range of 0.05-20 wt. %, preferably 0.1-10 wt. % of the whole composition. Compositions having a concentration lower than 0.05 wt. % exhibit incomplete herbicidal effect, while those having a concentration higher than 20 wt. % adversely affect the formation of foam.

Surfactants for forming are generally classified into cationic, anionic, nonionic and amphoteric surfactants. Any of these surfactants formed a foam in our experiments.

However, one or more surfactants selected from the group consisting of anionic and nonionic surfactants are used in the present invention due to good foam retention properties, water-solubility and compatibility with other components. The anionic surfactant is preferable used, an example of which may be calcium-dodecylbenzenesulfonate, alkylbenzenesulfonate alkaline earth metal salts, fatty acid alkaline earth metal salts, triethanolamine alkylsulfate, polyoxyethylene alkylphenyl ether sulfate, and sodium-alkyldiphenyletherdisulfate, preferably an alkaline salt of alkyl sulfosuccinic acid, an alkaline salt of polyoxyethylenealkylsulfric acid, an alkaline salt of polyoxyethylenealkylnaphthalenesulfonic acid; sodium salt thereof is preferably used. These preferable anionic surfactants tend to easily form a preparation (i.e. the original liquid) and have increased leaf surface depositing properties.

The nonionic surfactant used in the present invention may be one such as polyoxyethylene alkyl ether, sorbitan monooleate, sorbitan laurate, polyethylene glycol fatty acid ester, polyoxyethylene sorbitan fatty acid ester, and polyoxyethylene alkylphenyl ether.

The concentration of surfactants is in the range of 0.1-10 wt. %, preferably 1-10 wt. %. Compositions having a surfactant concentration lower than 0.1 wt. % do not easily form foam, while compositions having a surfactant concentration higher than 10 wt. % remain in soil and adversely affect the valuable plants which are to be cultivated after use.

Up to about 90 wt. % of water as a diluent is used to dissolve or suspend the herbicides and surfactants. The pH of the herbicidal foam composition is adjusted to within about 3-11, preferably to 3-6 or 8-11, since the stability of the herbicidal components is thereby increased. Suitable ions to adjust the pH are sodium, ammonium, phosphoric acid and organic acids. Potassium ion is not suitable due to occurrence of precipitation by salting-out; Calcium ion and magnesium ion are also not suitable since they may decompose the herbicidal components.

A solvent is used in the present invention to increase compatibility of the herbicidal components and to reduce the viscosity of the original liquid. The addition of a solvent also increases the stability of the herbicidal components, foam retention and leaf depositing properties.

The solvent as used in the present invention may be selected from the group consisting of a glycolether such as 1-methoxy-2-propanol, ethylene glycol and a mixture thereof, which increases the fluidity and compatibility and makes a preparation form easily. The concentration of each solvent is within the range of about 0.1 to 20 wt. %, preferably about 1 to 3 wt. %.

A foam controlling agent is used in the present invention to control foam stability and the texture of the foam. About 0.002 to 21 wt. % of the foam controlling agent as used in the present invention may be a $C_1$-$C_{10}$ alcohol, silicone oil and a mixture thereof. Silicone oil, rather than a $C_1$-$C_{10}$ alcohol, is effective to control the retention time of foam. The concentration of silicone oil may be about 0.001 to 0.1 wt. %, preferably about 0.002 to 0.02 wt. %, and that of a $C_1$-$C_{10}$ alcohol may be about 1 to 20%. A $C_1$-$C_{10}$ alcohol increases the fluidity of the foam and makes the texture of the foam rough as compared with silicone oil. An example of $C_1$-$C_{10}$ alcohol is ethanol and isopropyl alcohol.

Up to about 50 wt. % of liquefied petroleum gas is used as a propellant since water is used as a diluent.

The pH of the herbicidal foam composition of the present invention is adjusted to within about 3 to 11, preferably 8 to 10 in order to increase the stability of an aerosol can such as a tin can.

The herbicidal foam composition of the present invention may further comprise one or more stabilizing agents, spreading agents, thickeners, pastes, coloring agents, insecticides, germicides, fragrant agents or fertilizers.

A method which takes advantage of aerosol application and a method in which a sprayer apparatus is utilized are exemplified for foaming.

In the case of using an aerosol, a herbicidal solution comprising said herbicides, surfactants and diluent is enclosed in an aerosol container having a spraying device together with a propellant. The solution can easily be applied by pushing the button of the spraying apparatus. An example of a propellant is oil-soluble liquefied petroleum gas. As long as foam is formed, other materials or mixtures of the above-mentioned agents can be utilized. If the aerosol solution has a large polarity like water, a nonpolar propellant gas such as liquefied petroleum gas can advantageously be used, and if it has a small polarity, a polar gas such as diethyl ether can advantageously be used. Such formulations are called post-foaming since they produce stable foam after it clings to the target. The desirable concentration of propellant is no more than 50 wt. %, preferably 5-15 wt. % of the whole composition in case of liquefied petroleum gas; and no more than 2 wt. %, preferably 1-2 wt. % in case of compressed gases.

A spraying apparatus can be used to generate foam. In this case, a herbicidal solution is placed in a container equipped with a pressurizer such as a trigger-type sprayer, a manual pump or an electric pump, and is applied. The advantage in using a spraying apparatus is that the extent of mixing air with the herbicide solution can be adjusted to a desire level by handling the spraying mechanism in order to easily make a favorable foam. As long as foam is built up, any pressurizer can be used, for example, a manual pump, an electric pump, a spraying device using compressed gases, a container with a device which can generate foam, etc.

The herbicidal compositions according to the present invention can also be applied by either the Excell or Enviro systems. The Excell system takes advantage of the contracting property of an elastic material explained as follows: Flexible bags set inside a tubular material which can expand substantially in the radius direction, are pressure-packed with a flowing product to make the tubular material expand. When contraction of the tubular material occurs, the inside flowing product is forced out. For details, see Japanese Patent Public Disclosure No. 61-118163, Japanese Patent Publication No. 01-25626 (International Publication WO82/00780), and Japanese Patent Publication No. 02-60586 (International Publication WO82/02034).

The Enviro system utilizes gas generation through a chemical reaction. Expandable pressure bags containing chemical reagents which generate gases in reactions are placed in a container, which is divided into a product-involving area packed with a flowing product and a gas-generating area having several compartments. Chemicals such as an aqueous solution of sodium bicarbonate and citric acid solution placed in each compartment, start to react and generate gas (carbon dioxide gas in the above-mentioned case) in turn to make the flowing product gush out by the pressure of the generated gas. Details are seen in Japanese Patent Public Disclosure No. 64-84878, Japanese Patent Publication No. 01-111468 and Japanese Patent Publication No. 02-8780.

Herbicidal compositions of the present invention can be applied in the form of foam by the Excell or Enviro system. These systems, however, can merely spray a flowing product and have no foaming ability. Therefore it is necessary to add a low-boiling solvent having a boiling point of no higher than 20° C., such as n-pentane, n-butane, iso-pentane, isoprene, cyclopentane, and 2,2-dimethylpropane to the herbicidal composition by 1.0-20 wt. %, preferably 5-10 wt. % of the whole composition. Compositions having a concentration of low-boiling solvent lower than 1.0 wt. % cannot be sprayed to make a foam, while those of a concentration higher than 20 wt. % prevent the formation of a favored foam. Therefore, when the Excell or Enviro system is utilized, it is preferred that surfactants in an amount of 0.1-20 wt. % and a low-boiling solvent in an amount of 1.0-20 wt. % on the basis of the weight of the whole composition are added to the herbicide containing solution.

Addition of the above-mentioned low-boiling solvents shows good foaming even in preparations other than the Excell and Enviro systems. The concentration of the added solvent can be no higher than 1.0 wt. % in this case.

Herbicidal compositions according to the present invention can include a suspending agent such as carboxymethyl cellulose and ethylene glycol; an antifreezing agent such as ethylene glycol, ethyl cellosolve, butyl carbitol and 3-methyl-3-methoxybutanol; antiseptic agents such as P-hydroxy butylbenzoate to stabilize the active ingredients, and a rust preventive such as amino alcohol and morpholine to prevent the container from corroding. The addition of anionic surfactants such as monoglyceride and natural saponin exhibits good results on foaming. To stabilize the foam and maintain excellent texture, fatty acid amides, sulfate of Group VIII metals, sugars such as sorbitol and glucose, polyethylene glycols, animal or vegetable oils such as oleic acid, soy bean oil and beaf tallow, and kerosene can be added to the herbicidal composition. Addition of these stabilizers enables the formation of foam of an appropriate hardness (viscosity).

Herbicidal compositions according to the present invention can include a spreader such as surfactants, glycol ethers, sugars, casein, lime, paraffin and vegetable fibers to enable the herbicide to stick to weeds, and can also include colors or flavors to clearly enable visual discrimination of already-treated parts from untreated parts. Examples:

The following examples will illustrate the present invention. It is to be understood that the invention is not limited to these examples.

The chemical names of compounds used in the examples and Tables are as follows:

| COMMON NAME | CHEMICAL NAME |
| --- | --- |
| Bialaphos: | L-2-amino-4-[(hydroxy)(methyl)-phosphinol]-butyryl-L-alanyl-L-alanin sodium salt. |
| Glufosinate: | ammonium-DL-homoalanin-4-yl(methyl)phosphinate. |
| Glyphosate: | isopropylamine salt of N-(phosphonomethyl)-glicine. |

EXAMPLES 1-28

The Examples are preparations of herbicidal compositions applied by an aerosol container.

Various herbicides, surfactants and propellants were compounded according to the chemical compositions shown in Tables 1 and 2. A herbicide and a surfactant were mixed to give a homogeneous solution or a suspension followed by addition of other components such as an antifreeze and a stabilizer. The mixture became a uniform liquid or a suspension. A diluent (water) was added thereto to obtain a uniform emulsion or a suspension. The resultant mixture was pressure-packed in an aerosol can together with a propellant to prepare a foam-forming aerosol herbicidal composition.

Each aerosol herbicide prepared by the same procedure as described above was examined to determine the following properties:

(I) Test on the Volatility of the Original Liquid (wt. %)

The test results were obtained by calculating the reduced weight after the liquid stood still (at a temperature of 25° C.) for 24 hours.

(II) Viscosity of the Original Liquid (mPa.s)

The measurement was carried out using B type viscosimeter (apparent viscosity).

(III) Fluidity of the Original Liquid (Inspection on Thixotropy)

Since a liquid containing surface active agents is a non-Newtonian liquid, kinematic viscosity and static viscosity are sometimes different from each other. In the case of a non-Newtonian liquid, if the viscosity measured under the standing condition of the liquid is compared with the viscosity measured immediately after the mixing by means of stirring, we found that the viscosity measured immediately after the mixing by means of stirring is much lower (but, in the case of a Newtonian liquid like water, it is impossible to find such phenomenon). Since only the apparent viscosity of a non-Newtonian liquid can be measured using a B type viscosimeter, the inspection with respect to variation of the viscosity was executed by eye-measurement, and then the marks ⊚, ○ and Δ were assigned depending on the extent of the difficulty of preparing the original liquid. In the case of Δ, it is possible to prepare the original liquid.

(IV) Compatibility of the Original Liquid

The compatibility of every component excluding water which was used as a diluent was inspected by eye-measurement. Where there was a separated layer the mark × is given, where there was no such separated layer the mark given is ⊚.

(V) Water-Solubility of the Original Liquid

The compatibility of every component including water which was used as a diluent was inspected by eye-measurement. Where the separated layer was clear the mark × is given, where such separated layer was not clear the mark Δ is given, where there was no such separated layer but an emulsified state (a white-turbid and homogeneous liquid) appeared, the mark ○ is given. Where there was no separated layer but a meltable state (a transparent homogenous liquid) appeared, the mark ⊚ is given.

(VI) The foam was judged by the retention times of foam structures after spraying onto a floor having a size of 1×1 m for five seconds (equivalent to about 20 g). The results were scored as follows:

| ⊚ | foam retention time >5 min. (excellent) |
| --- | --- |
| ○ | 2-5 min. (fair) |
| Δ | 1-2 min. (not good) |
| × | 0-1 min. (bad) |

Herbicidal effects were judged by the vegetation rates (fraction of covered ground with weeds) at the fourth week after the herbicidal formulations were applied onto the ground having a size of 1×1 m for five seconds (equivalent to about 20 g). The results were scored as follows:

| | |
|---|---|
| ⊚ | vegetation rate <20%. (excellent) |
| ○ | 20–40%. (fair) |
| Δ | 40–60%. (not good) |
| x | >60%. (bad) |

(VII) Adhesion on the Leaf Surface

An aerosol container was attached to an automatic aerosol sprayer (manufactured by Yamada Seiki Seisakusho). The herbicidal composition was sprayed downward from the apparatus toward a 50×50 cm test paper fixed with four-corner-tacks on a 50×50 cm wood frame laid on the floor. The vertical distance between the sprayer and the target was 20 cm. The spraying duration was 1 sec. The difference between the initial and the final weight of the container was determined and used in the calculation of the theoretical deposited amount (sprayed amount × active agent concentration). Then the percent deposit (observed value/theoretical value × 100) was computed. The calculated values are shown in Tables 1 and 2.

(VIII) Herbicidal Effect

The herbicidal effect was evaluated by first spraying the herbicide for 5 seconds (corresponding to about 20 g) onto a plot of ground of 1×1 m, then by making use of the plant-covered ratio (a proportion indicating the ratio of the herb-covered ground) in the fourth week, and using the following judgment standards. Where the plant-covered ratio was less than 20% (very good) the mark ⊚ is given, where the plant-covered ratio was 20–40% (good) the mark ○ is given, where the plant-covered ratio was 40–60% (not so good) the mark Δ is given, and where the plant-covered ratio was greater than 60% (bad) the mark given is ×.

ADVANTAGES OF THE INVENTION

As stated above, the herbicidal foam compositions of the present invention possess the merits of solid and liquid agents. The present invention therefore provides the following advantages:

(a) The herbicidal foam composition of the present invention has excellent volatility, fluidity, compatibility, water-solubility of the original liquid, foam retention, foam adhesion on the leaf surface (a cuticular layer) and herbicidal effects.

(b) In the case of using herbicides for stem and leaves, the compositions of the present invention easily deposit on weeds thus increasing the herbicidal action.

(c) In the case of using the herbicides for stems and leaves and for soil, the application of the herbicidal foam composition can be visually confirmed, thus preventing excess application.

(d) In the case of using the herbicides for stems and leaves, the foam gradually descends along the surface of leaves to which the herbicidal foam composition has been applied, thereby enabling uniform application of the agent over the weed.

(e) The compositions of the present invention are safer to use due to reduce scattering or drifting.

(f) The present invention does not result in an unsightly appearance since the foam gradually disappears.

(g) The compositions of the present invention can be formed into an aerosol formulation and easily used with a spraying apparatus.

(h) The herbicidal foam compositions of the present invention can be formed with the Enviro System or the Excell System.

(i) Additional agents such as fragrances, insecticides, germicides and agents for controlling the growth of plants agents can be utilized.

TABLE 1

| | Examples | | | | |
|---|---|---|---|---|---|
| | 1 | 2 | 3 | 4 | 5 |
| Bialaphos | 2.50 | 2.50 | 2.50 | 2.50 | 2.50 |
| Sodium dioctylsulfosuccinate | 1.47 | 1.47 | 0.73 | | |
| Sodium polyoxyethylene (2) laurylsulfate | 2.93 | 3.66 | | | |
| Sodium laurylsulfate | | | 3.66 | 2.93 | |
| Sodium polyoxyethyleneoctyl naphthalene sulfonate | | | | | 2.93 |
| 1-methoxy-2-propanol | 1.47 | 1.47 | | 1.47 | |
| Ethylene glycol | | 0.29 | | | |
| Isopropyl alcohol | | | 1.76 | | 1.32 |
| Octyl alcohol | | | | | 0.15 |
| Silicone oil | 0.006 | 0.006 | 0.006 | 0.006 | 0.006 |
| Blue No. 1 | 0.0015 | 0.0015 | 0.0015 | 0.0015 | 0.0015 |
| Liquefied petroleum gas | 12.09 | 12.09 | 12.09 | 12.09 | 12.09 |
| Water (ion-exchanged water) | bal. | bal. | bal. | bal. | bal. |
| Total | 100 | 100 | 100 | 100 | 100 |
| Volatility | 25.0 | 27.0 | 33.4 | 26.5 | 29.2 |
| Viscosity | 66 | 106 | 80 | 95 | 72 |
| Fluidity | ○ | ○ | ○ | ○ | Δ |
| Compatibility | ⊚ | ⊚ | ⊚ | ⊚ | ⊚ |
| Water-solubility | ⊚ | ⊚ | ⊚ | ⊚ | ⊚ |
| Foam retention | ⊚ | ⊚ | ⊚ | ⊚ | ⊚ |
| Leaf surface depositing properties | ⊚ | ⊚ | ⊚ | ⊚ | ○ |
| Herbicidal effect | ⊚ | ⊚ | ⊚ | ⊚ | ⊚ |
| | Examples | | | | |
| | 6 | 7 | 8 | 9 | 10 |
| Bialaphos | 2.50 | 2.50 | 2.50 | 2.50 | 2.50 |
| Sodium polyoxyethyleneoctyl naphthalene sulfonate | 2.93 | | | | |
| Sodium polyoxyethylenelauryl naphthalene sulfonate | | 2.93 | 2.93 | 2.93 | |
| Polyoxyethylene (20) sorbitan octylether | | | | | 2.93 |

TABLE 1-continued

|  | 6 | 7 | 8 | 9 | 10 |
|---|---|---|---|---|---|
| Isopropyl alcohol | 1.47 | 1.32 | 1.47 | 1.76 | 1.76 |
| Octyl alcohol |  | 0.15 |  |  |  |
| Silicone oil | 0.006 | 0.006 | 0.006 | 0.006 | 0.006 |
| Blue No. 1 | 0.0015 | 0.0015 | 0.0015 | 0.0015 | 0.0015 |
| Liquefied petroleum gas | 12.09 | 12.09 | 12.09 | 12.09 | 12.09 |
| Water (ion-exchanged water) | bal. | bal. | bal. | bal. | bal. |
| Total | 100 | 100 | 100 | 100 | 100 |
| Volatility | 32.5 | 27.2 | 29.5 | 35.5 | 33.6 |
| Viscosity | 65 | 93 | 83 | 72 | 35 |
| Fluidity | Δ | Δ | Δ | Δ | ⊚ |
| Compatibility | ⊚ | ⊚ | ⊚ | ⊚ | Δ |
| Water-solubility | ⊚ | ⊚ | ⊚ | ⊚ | ○ |
| Foam retention | ⊚ | ⊚ | ⊚ | ⊚ | ○ |
| Leaf surface depositing properties | ○ | ○ | ○ | ○ | ○ |
| Herbicidal effect | ⊚ | ⊚ | ⊚ | ⊚ | ⊚ |

|  | Examples | | | |
|---|---|---|---|---|
|  | 11 | 12 | 13 | 14 |
| Bialaphos | 2.50 | 2.50 | 2.50 | 2.50 |
| Polyoxyethylene (20) sorbitan octylether | 2.93 | 2.93 |  |  |
| Polyoxyethylene (20) sorbitan laurylether |  |  | 2.93 | 2.93 |
| Isopropyl alcohol | 1.32 | 1.47 | 1.32 | 1.47 |
| Octyl alcohol | 0.15 |  | 0.15 |  |
| Silicone oil | 0.006 | 0.006 | 0.006 | 0.006 |
| Blue No. 1 | 0.0015 | 0.0015 | 0.0015 | 0.0015 |
| Liquefied petroleum gas | 12.09 | 12.09 | 12.09 | 12.09 |
| Water (ion-exchanged water) | bal. | bal. | bal. | bal. |
| Total | 100 | 100 | 100 | 100 |
| Volatility | 25.4 | 32.0 | 24.4 | 31.2 |
| Viscosity | 53 | 45 | 55 | 30 |
| Fluidity | ○ | ○ | ○ | Δ |
| Compatibility | Δ | Δ | Δ | Δ |
| Water-solubility | ○ | ⊚ | ⊚ | ⊚ |
| Foam retention | ○ | Δ | ⊚ | ⊚ |
| Leaf surface depositing properties | ○ | Δ | ○ | ○ |
| Herbicidal effect | ⊚ | Δ | ⊚ | ⊚ |

TABLE 2

|  | Examples | | | | |
|---|---|---|---|---|---|
|  | 15 | 16 | 17 | 18 | 19 |
| Bialaphos | 2.50 | 2.50 | 2.50 | 2.50 | 2.50 |
| Sodium dioctylsulfosuccinate | 1.47 | 1.47 | 1.47 | 1.47 | 1.47 |
| Sodium polyoxyethylene (2) laurylsulfate | 2.93 | 2.93 | 2.93 | 2.93 | 2.93 |
| 1-methoxy-2-propanol | 1.47 | 1.47 |  | 1.47 | 1.47 |
| 3-methoxy butanol |  |  | 1.47 |  |  |
| Sodium hydroxide | 5 |  |  |  |  |
| Ammonium tertiary phosphate |  | 5 | 5 |  |  |
| Ammonia water |  |  |  | 5 |  |
| Citric acid |  |  |  |  | 5 |
| Silicone oil | 0.006 | 0.006 | 0.006 | 0.006 | 0.006 |
| Blue No. 1 | 0.0015 | 0.0015 | 0.0015 | 0.0015 | 0.0015 |
| Liquefied petroleum gas | 12.09 | 12.09 | 12.09 | 12.09 | 12.09 |
| Water (ion-exchanged water) | bal. | bal. | bal. | bal. | bal. |
| Total | 100 | 100 | 100 | 100 | 100 |
| Fluidity | ○ | ○ | Δ | ○ | ○ |
| Compatibility | ⊚ | ⊚ | ⊚ | ⊚ | ⊚ |
| Water-solubility | ⊚ | ⊚ | Δ | ⊚ | ⊚ |
| Foam retention | ⊚ | ⊚ | ⊚ | ⊚ | ⊚ |
| Herbicidal effect | ⊚ | ⊚ | ⊚ | ⊚ | ⊚ |

|  | Examples | | | | |
|---|---|---|---|---|---|
|  | 20 | 21 | 22 | 23 | 24 |
| Bialaphos | 1.25 | 1.25 | 1.25 | 1.25 |  |
| Glufosinate | 1.25 |  |  |  | 2.50 |
| Glyphosate |  | 1.25 | 1.25 | 1.25 |  |
| Sodium dioctylsulfosuccinate |  |  |  |  | 0.73 |
| Sodium polyoxyethylene (2) laurylsulfate | 2.93 | 2.93 | 2.93 | 2.93 |  |
| Sodium laurylsulfate |  |  |  |  | 3.66 |
| 1-methoxy-2-propanol | 1.47 | 1.47 | 1.47 | 1.47 |  |
| Isopropyl alcohol |  |  |  |  | 1.76 |
| Ammonium tertiary phosphate | 5 | 5 | 5 | 5 |  |
| Silicone oil | 0.006 | 0.002 | 0.006 | 0.020 | 0.006 |
| Blue No. 1 | 0.0015 | 0.0015 | 0.0015 | 0.0015 | 0.0015 |
| Liquefied petroleum gas | 12.09 | 12.09 | 12.09 | 12.09 | 12.09 |
| Water (ion-exchanged water) | bal. | bal. | bal. | bal. | bal. |
| Total | 100 | 100 | 100 | 100 | 100 |
| Fluidity | ○ | ○ | ○ | ○ | ○ |
| Compatibility | ⊚ | ⊚ | ⊚ | ⊚ | ⊚ |

TABLE 2-continued

|  | 25 | 26 | 27 | 28 |
|---|---|---|---|---|
| Water-solubility | ⊚ | ⊚ | ⊚ | ⊚ | ⊚ |
| Foam retention | ⊚ | c | ⊚ | ○ | ⊚ |
| Herbicidal effect | ⊚ | ⊚ | ⊚ | ⊚ | ⊚ |

| | Examples | | | |
|---|---|---|---|---|
| | 25 | 26 | 27 | 28 |
| Glufosinate | 2.50 | 2.50 | | 2.50 |
| Glyphosate | | | 2.50 | |
| Sodium laurylsulfate | | 2.93 | | 2.93 |
| Sodium polyoxyethyleneoctylnaphthalene-sulfonate | 2.93 | | | |
| Sodium polyoxyethylenelaurylnaphthalene-sulfonate | | | 2.93 | |
| 1-methoxy-2-propanol | | 1.47 | | 1.47 |
| Isopropyl alcohol | 1.32 | | 1.32 | |
| Octyl alcohol | 0.15 | | 0.15 | |
| Silicone oil | 0.006 | 0.006 | 0.006 | 0.006 |
| Blue No. 1 | 0.0015 | 0.0015 | 0.0015 | 0.0015 |
| Liquefied petroleum gas | 12.09 | 12.09 | 12.09 | 12.09 |
| Water (ion-exchanged water) | bal. | bal. | bal. | bal. |
| Total | 100 | 100 | 100 | 100 |
| Fluidity | Δ | ○ | Δ | ○ |
| Compatibility | ⊚ | ⊚ | ⊚ | ⊚ |
| Water-solubility | ⊚ | ⊚ | ⊚ | ⊚ |
| Foam retention | ⊚ | ⊚ | ⊚ | ⊚ |
| Herbicidal effect | ⊚ | ⊚ | ⊚ | ⊚ |

What is claimed is:

1. A herbicidal foam composition comprising, on the basis of the total weight of the composition,
   (a) about 0.05 to 20% of a herbicide selected from the group consisting of Bialaphos, Glufosinate, Glyphosate and a mixture thereof,
   (b) about 0.1 to 10% of an anionic surfactant selected from the group consisting of alkylsulfosuccinate alkaline salts, polyoxyethylenealkylsulfate alkaline salts, polyoxyethylenealkylnaphtalenesulfonate alkaline salts and a mixture thereof,
   (c) about 0.1 to 20% of a solvent selected from the group consisting of glycolethers and a mixture thereof,
   (d) about 0.002 to 21% of a foam controlling agent selected from the group consisting of silicone oil, a $C_1$-$C_{10}$ alcohol and a mixture thereof,
   (e) up to about 90% of water as a diluent and
   (f) up to about 50% of liquefied petroleum gas as a propellant, the pH of said composition being adjusted to within about 3-11.

2. The composition of claim 1 wherein said glycolether is selected from the group consisting of 1-methoxy-2-propanol, ethylene glycol and a mixture thereof.

3. The composition of claim 2 wherein said glycolether is incorporated in an amount of 1 to 3%.

4. The composition of claim 1 wherein said silicone oil is incorporated in an amount of 0.001 to 0.1%.

5. The composition of claim 1 wherein said silicone oil is incorporated in an amount of 0.002 to 0.02%.

6. The composition of claim 1 wherein said $C_1$-$C_{10}$ alcohol is incorporated in an amount of 1 to 20%.

7. The composition of claim 1 further comprising one or more stabilizing agents, spreading agents, thickeners, pastes, coloring agents, insecticides, germicides, fragrant agents or fertilizers.

8. The composition of claim 1 wherein the pH of said composition is adjusted to within about 8-10.

* * * * *